United States Patent [19]

Heine et al.

[11] 4,215,678

[45] Aug. 5, 1980

[54] ENDOSCOPE

[75] Inventors: Helmut A. Heine; Werner E. Erfurt, both of Herrsching, Fed. Rep. of Germany

[73] Assignees: Propper Manufacturing Co., Inc., Long Island City, N.Y.; Heine Optotechnik GmbH & Co. KG, Herrsching, Fed. Rep. of Germany

[21] Appl. No.: 772,500

[22] Filed: Feb. 28, 1977

[30] Foreign Application Priority Data

Aug. 13, 1976 [DE] Fed. Rep. of Germany ....... 2636510

[51] Int. Cl.$^2$ ............................................ A61B 1/06
[52] U.S. Cl. ................................. 128/6; 350/276 SL
[58] Field of Search ............................. 128/3–8; 350/96 D, 96.26, 276 SL

[56] References Cited

U.S. PATENT DOCUMENTS

| 2,699,770 | 1/1955 | Fourestier | 128/6 |
| 2,843,112 | 7/1958 | Miller | 128/6 |
| 2,922,415 | 1/1960 | Campagna | 128/4 |
| 3,068,739 | 12/1962 | Hicks et al. | 128/6 |
| 3,071,129 | 1/1963 | Wasserman | 128/6 |
| 3,261,349 | 7/1966 | Wallace | 128/6 |
| 3,261,356 | 7/1966 | Wallace | 128/6 |
| 3,417,746 | 12/1968 | Moore et al. | 128/6 |
| 4,048,988 | 9/1977 | Regenbogen | 128/4 |

FOREIGN PATENT DOCUMENTS

| 605025 | 9/1960 | Canada | 128/6 |
| 1117256 | 11/1961 | Fed. Rep. of Germany | 128/6 |
| 551146 | 2/1943 | United Kingdom | 128/6 |

Primary Examiner—Robert W. Michell
Assistant Examiner—Arthur S. Rose
Attorney, Agent, or Firm—Amster, Rothstein & Engelberg

[57] ABSTRACT

An endoscope includes a light conducting outer tube and a light absorbing inner tube, with the inner tube being located concentric with the outer tube and being spaced a distance radially inwardly from the outer tube so as to maintain total internal reflection in the light conducting material of the outer tube.

10 Claims, 10 Drawing Figures

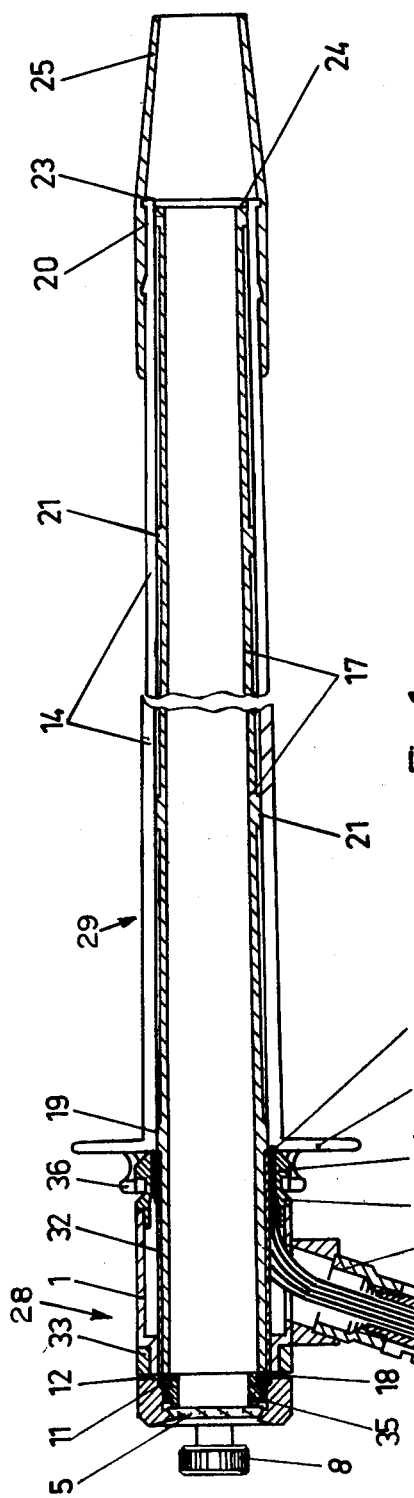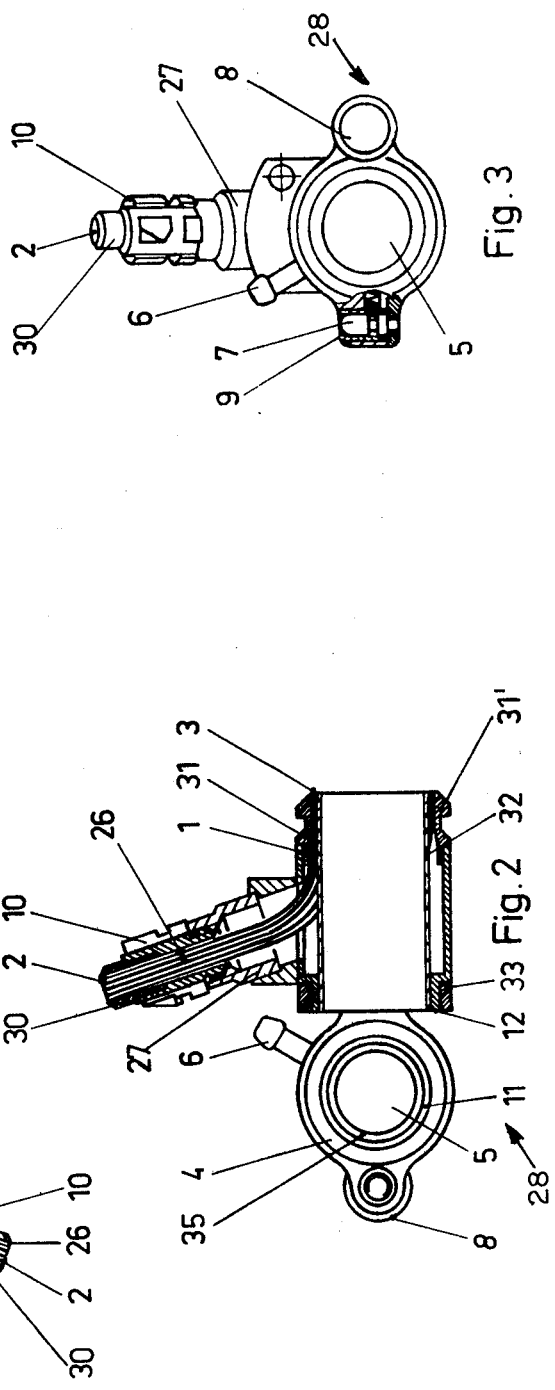

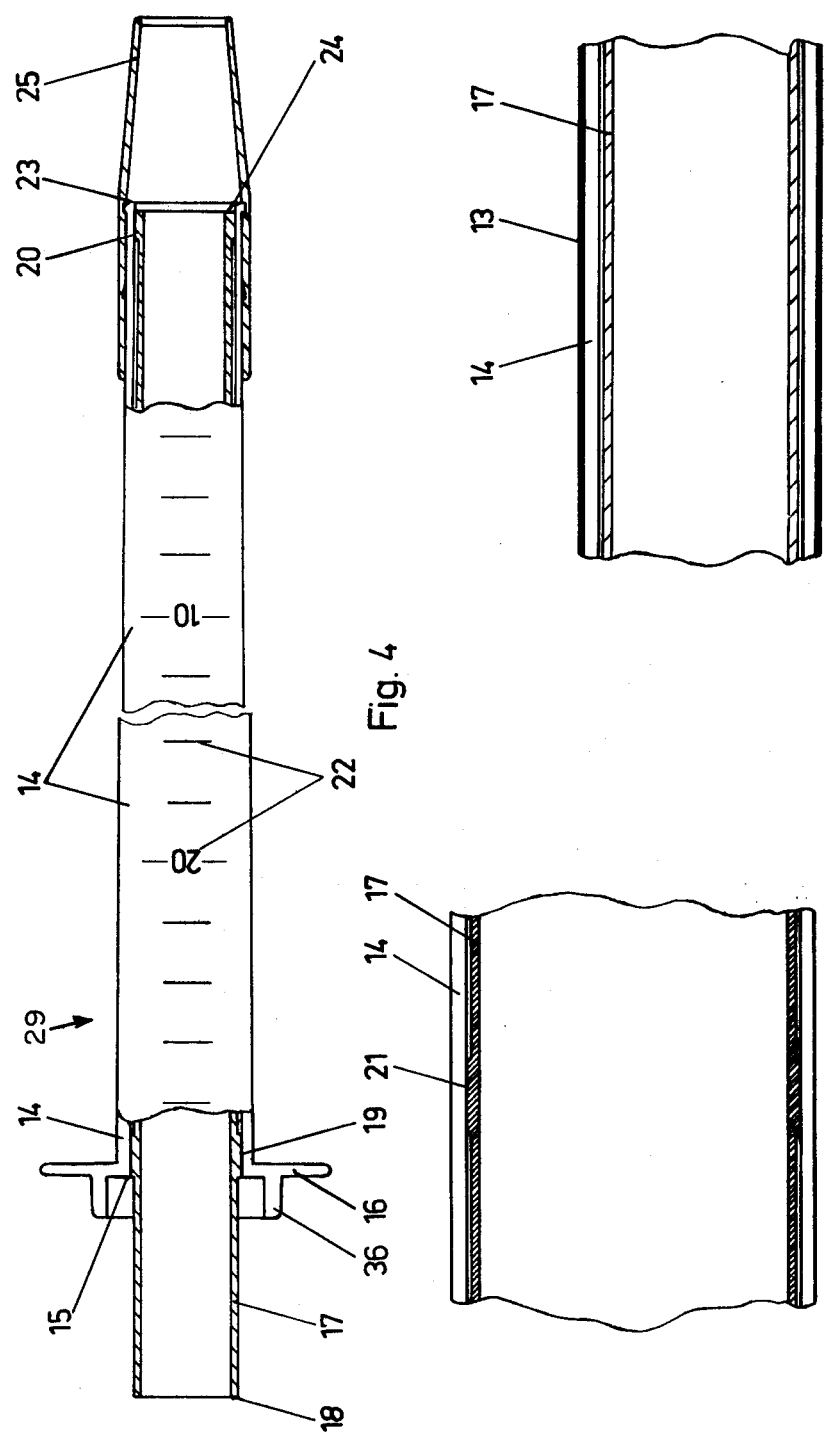

ENDOSCOPE

The present invention relates to an endoscope, particularly a rectoscope, comprising a head and a detachable tube which is introduced into the body cavity to be examined, for example, the rectum. The observation of the object to be examined proceeds through the head and tube, with the endoscope containing an illumination device to ensure sufficient illumination of the object to be observed.

Endoscopes of this type have been known for years; in the book "Die Proto-Sigmoscopie" (Leipzig 1910), H. Strauss describes a retoscope where the tube is made of metal and a small incandescent lamp is used at the distal end of the tube.

The question of the most advantageous design of the illuminating arrangement, understandably, has played a considerable part from the outset. The incandescent lamp located distally in the tube impedes the field of vision and, in case of damage to the lamp, endangers the patient. Swiss Pat. No. 208,643 describes endoscopes made of a tube of transparent material, with total internal reflection occurring at the walls so that the light is conducted down the tube walls, and an illuminating arrangement located at the proximal end of the tube. As light conducting fiber became known and available, they were introduced in the endoscopy art. U.S. Pat. No. 3,261,349 describes such endoscopes using light conducting fibers.

Originally, metal tubes were exclusively used for manufacturing the tubes, until, through the above-cited Swiss patent, light conducting tubes made of glass or synthetic material were introduced.. The German Pat. No. 1,566,179 describes an endoscope comprising a head into which light-conducting fibers are inserted; at the proximal end, these fibers are bunched into a circular cross section while at the distal end, this fiber bundle has an annular cross section. Into this headpiece, one can insert a tube of transparent plastic in whose walls the light coming from the head is conducted by total reflection to the distal end where it leaves the tube and serves to illuminate the object. Ithas been proposed there to make the tube and other parts coming into contact with the patient during examination, (e.g., the obturator introduced from the proximal end) of reasonably priced synthetic material so that these parts can be discarded after each examination so that cleaning and sterilizing is not necessary. Instruments like the one described in the German Pat. No. 1,566,179 have a distinct disadvantage which is extremely troublesome in practical use.

The light coming from the head and carried between the walls of the light-conducting tube is totally internally reflected by the tube walls only as long as these walls are in a medium of lower optical index of refraction. Since in the practical use of endoscopes, the walls of the examined human organ, e.g., the walls of the rectum, frequently lie against the tube, and since this almost always involves wet mucous membranes, this requirement is no longer satisfied. At those locations where portions of organs lie against the outside wall of the light-conducting tube, total internal reflection no longer takes place; rather, the light passes through the tube wall and illuminates these organ portions.

As a result, light penetrates from the illuminated organ portions through the transparent walls of the tube and, partially by reflections at the inside walls of the tube, gets back to the eye of the observer. The consequence of this interfering light is, that, for one, the observer is somewhat blinded, i.e., his eye by accommodation adapt to the larger total light flux, hence to the sum of the light fluxes from the object and the interfering light, so that the image of the object appears darker to the observer, and that, secondly, the contrasts of the image of the object seen become much worse through the superimposed scattered light. Light gets to the observer from the object so that he can see the object. But light from the object also get to the inside walls of the tube and is reflected there, in accordance with optical reflection laws, in the direction toward the proximal end of the instrument and, to a great extent, to the eye of the observer. This interfering light causes the same phenomena as was described above for the interfering light of the organ portions lying against the tube wall.

Attempts have already been made on metal tubes to alleviate this problem by frosting, dulling or coating the inside surface of the tube or by placing flat threads on it. However, these attempts have not led to a satisfactory result. In addition, such measures impair the usability of the tube because cleaning and sterilizing is hindered greatly. Such disadvantages are not present with plastic tubes serving as light conductors since they can be discarded after being used once. However, they impair the usefulness of the tube in another way, because a smooth outside and inside surface is necessary for the tubes functioning as light conductor. If the inside surface of the tube were roughened, an appreciable portion of the light passing through the tube would reach the eye of the observer as scattered light and would not be available for observing the object. A tube of the previously known type where outside and inside surface must be transparent and completely smooth in order to ensure total reflection, makes the observation of the object extremely difficult, owing to the two types of interfering light, and reduces detail recognizability.

It is the object of the present invention to avoid the disadvantages of the known endoscopes. In particular, an endoscope of the type described in the preface of patent claim 1 of German Pat. No. 1,566,179 is to be constructed in such a way that the interfering light of both types, the one reflected from the organ walls lying against the outside wall of the tube, and the light reflected from the inside wall of the tube, coming from the organ, are kept as much as possible away from the eye of the observer so that he virtually sees only the light coming directly from the illuminated object. An attempt is made to achieve extremely simple handling and low manufacturing cost for the tube so that it can be discarded after a single usage.

The object of the present invention is achieved by an inner tube of light-absorbing, preferably black material, located concentric in the main tube and at a distance from its inside surface. With the endoscope in accordance with the present invention, the light coming from the organ is completely blocked by the inside tube from the eye of the observer and the light coming from the object, insofar as it strikes the inside surface of the inner tube, is extensively absorbed by it and not reflected to the eye of the observer. The air in the space between the outer and the inner tube has a lower index of refraction than the synthetic material of the outer tube, so that total reflection on the inside surface of the light conducting outer tube is ensured and virtually no light gets lost to the inner tube on the way between the proximal and the distal end of the tube.

In order to keep the proportion of light transmitted from the outside tube to the inner tube as low as possible, spacers are provided between the outer and inner tube, with the spacer areas bounding the tubes being small in comparison to the surfaces facing each other.

The spacers may be point-like, ring-like or ring-segment-like. They are preferably made part of the outer or inner tube.

In order to avoid loss of light through the outer tube to the organ walls lying against the outside wall of the outer tube, the outside surface of the outer tube is coated with a thin layer of a material whose index of refraction is lower than that of the outer tube.

Particularly convenient and clean handling can be achieved if the inner tube on its proximal side is extended beyond the outer tube to the proximal end of the head and a cover is attached to the proximal end of the head; the gasket of the cover lies against the proximal end surface of the inner tube.

A particularly expedient embodiment results if the inside wall of the outer tube and the outside wall of the inner tube are slightly conic, with the larger diameter on the proximal side, and the contact surfaces are dimensioned so that inner tube and outer tube, after being assembled, are self-locking.

The invention is explained in more detail by the embodiments shown in the drawing, wherein:

FIG. 1 shows a lengthwise section through an endoscope in accordance with the invention;

FIG. 2 shows a lengthwise section through the head with the cover flipped open;

FIG. 3 shows a partially sectioned top view of the head, seen from the viewing side;

FIG. 4 shows the partially sectioned view of a tube in accordance with the present invention;

FIGS. 5 and 6 show partial sections of tubes in accordance with the present invention.

Figure 7:
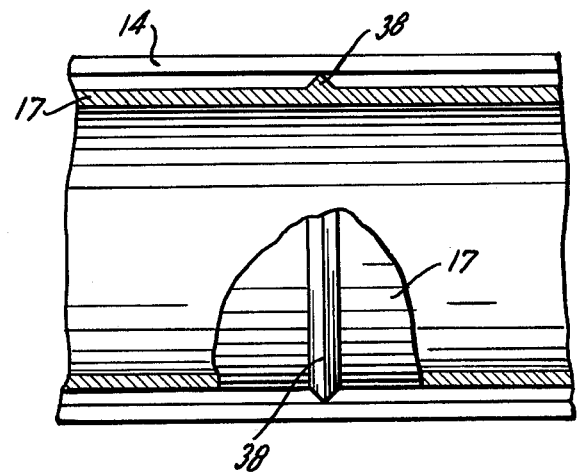
FIG. 7 is a cross-sectional view of a tube in accordance with an embodiment of the invention with the inner tube shown partially in elevation.

According to FIG. 1, the endoscope comprises a head 28 and a tube 29.

The head 28 comprises an outer housing 1 with a projection 27 through which a light fiber bundle 26 is inserted into the head 1. A connection piece 10 is inserted in projection 27 and serves as connection for a lamp housing or light conductor cable (not shown). In connection piece 10, a guide sleeve 30 is inserted by means of which the circular proximal end 2 of the light conductor fiber bundle 26 is held.

At the distal end, on the right-hand side, in FIG. 1, of housing 1, a coupling ring 31 is fastened. It serves, together with a sleeve 32 located in housing 1, as support for the annular distal end 3 of the light conductor fiber bundle 26, and for fastening the tube 29 yet to be described in detail.

On the proximal end of housing 1, shown on the left side of FIG. 1, a holding ring 33 is mounted on which a cover 4 is attached by means of a pin 7 and a bore 9 with a detenting arrangement (FIGS. 2, 3). The cover is pivotable and can be removed. On the holding ring 33 side facing the hinge formed by the pin 7 and the bore 9 an eye (not shown) is provided with a tapped hold (not shown) into which a screw 8 can be threaded for locking cover 4. Cover 4 has a holder ring 35 which, together with the housing of cover 4, serves for mounting a magnifying glass or face plate 5, in the center opening of cover 4, for mounting a gasket ring 11. The cover 4 has a insufflator inlet 6 through which an overpressure can be built up inside the endoscope when the cover 4 is closed.

The tube 29 comprises an outer tube 14 and an inner tube 17. The proximal end of the outer tube 14, made of transparent synthetic material, has a protective shield 16, which connects to a connection piece 36 overlapping the coupling ring 31. Head 28 and tube 28 are coupled disconnectably by means of coupling elements 31, attached to coupling ring 31, and associate grooves in connection piece 36. In FIG. 1, the inner tube 17 is extended towards the left beyond the outer tube 14 to the proximal end surface 12 of housing 1 of head 28 where at its proximal end there is a sealing surface 18 (FIG. 4) which, together with the gasket ring 11 provides a tight connection between cover 4 and the inner tube 17.

A spacer sleeve 25 is mounted on the distal end of the outer tube 14.

Adjacent to the distal annular end 3 (FIG. 2) of the light conductor fiber bundle 26 is the light entry surface 15 of outer tube 14. The spacer sleeve 25 projects beyond the light exit surface 23 of outer tube 14 and keeps the light exit surface 23 at a distance from the organ to be examined so the light can spread over its entire area (FIG. 4). The outside surface of outer tube 14, according to FIG. 6, may have a thin coat 13 of a material whose index of refraction is lower than that of the material of the outer tube 14.

Figure 8:
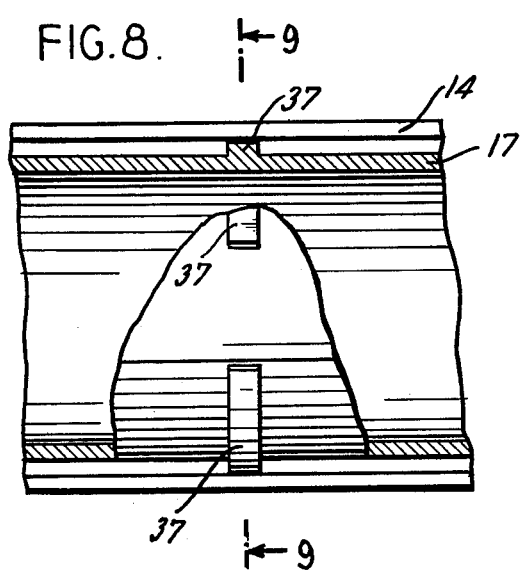
FIG. 8 is a cross-sectional view of a tube in accordance with a further embodiment of the invention with the inner tube shown partially in elevation.
Figure 9:
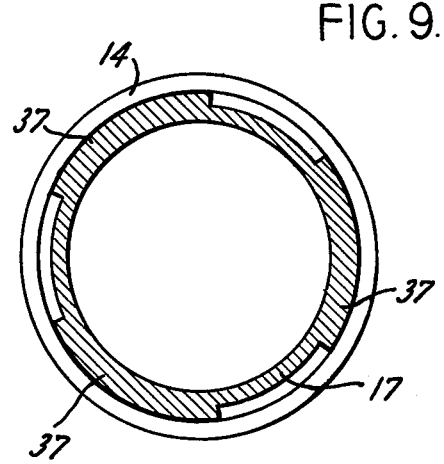
FIG. 9 is a cross-sectional view taken along line 9—9 in FIG. 8.
Figure 10:
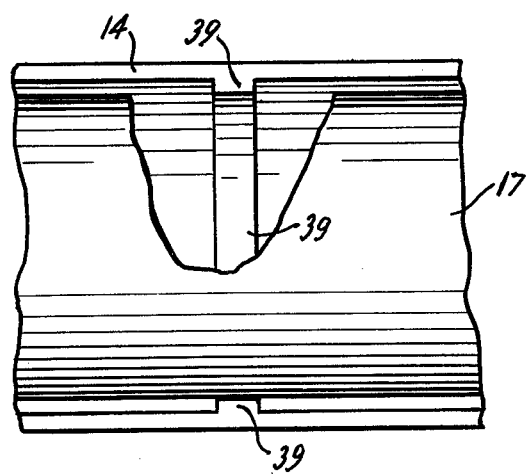
FIG. 10 is a cross-sectional view of the tube in accordance with an embodiment of the invention with the inner tube shown in elevation and partially broken away.

According to FIGS. 1, 4 and 5, the inner tube 17 has ribs 19, 20 and 21 protruding to the outside which ribs keep the two tubes spaced apart so that they contact each other along a surface as small as possible. Depending on the length of the tubes, two or more ringshaped ribs may be provided as spacers. With the embodiment shown in FIGS. 1 to 6 of the drawing, an annulus-shaped rib 19, 20 or 21 is located at the proximal and distal end of the two tubes and in the middle between the two ends. Instead of ribs 19, 20 and 21, other spacers may also be used between the two tubes. For example, dot-like warts or circular-segment shaped ribs may be formed on the outer and inner tube. FIGS. 8 and 9 show circular-segment-shaped ribs 37 and FIG. 10 shows an annular rib 39 on the outer tube. Also, instead of the wide contact surface shown in the figures, the ribs may have a narrower contact surface or a pointed profile such as rib 38 in FIG. 7.

The distal end 24 of inner tube 17 is preferably located a small distance behind the light exit surface.

In usage, a tube 29 is attached to head 28; the coupling ring 31 and the connection piece 36 provide a tight connection which is supported by the extension of the inner tube 17 made of light-absorbing material. The cover 4 is opened, and from the proximal end of head 28 a obturator (not shown) is introduced into the interior of the endoscope until it projects from the distal end. The obturator closes the opening at the distal end during insertion and thus prevents dirt from getting inside the instrument when inserting it into the cavity to be examined. In addition, a lamp housing or fiber optic cable is attached to the connection piece 10. Now the endoscope can be inserted into the cavity to be examined, with the insertion depth being read by graduations and numbers 22 located on the inside of outer tube 14. After the endoscope has been sufficiently inserted into the cavity to be examined, the obturator is pulled out and the light source is turned on. The light propagates from the distal end of the light conductor fiber bundle 26 and the light entry surface 15 of outer tube 14 with total reflection at the wall surfaces of outer tube 14 to its light exit surface 23 and illuminates the cavity to be examined at the free opening of the spacer sleeve.

The cavity can be observed and examined through the opening at the proximal end of head 28. Virtually only that light strikes the eye of the observer which has been reflected by the organ in front of the free opening of spacer sleeve 25. Hence the ratio of useful to interfering signal is very high.

If, desired, the cover 4 may be closed and an overpressure can be built up inside the endoscope by means of a insufflator connected to the insufflator inlet.

After the examination, the entire tube and the obturator can be discarded so that there are no costs for sterilizing. If desired, these parts may be manufactured from a material which can be sterilized and thus used again.

What is claimed is:

1. An endscope for examining body cavities comprising, an endoscope head, a rigid outer tube of light conducting material having a distal end and a proximal end, said proximal end being adapted to be secured to said head and said distal end being adapted to be inserted into a body cavity, illumination means in said head for directing light into the light conducting material of said outer tube at the proximal end thereof, said outer tube conducting light from said proximal end to said distal end to illuminate said body cavity while permitting the passage of unwanted transverse light intermediate said proximal and distal ends, an inner tube defining a viewing passageway and being dimensioned to permit observation of the interior of said body cavity therethrough, said inner tube being of a material such that it prevents extraneous light from entering said viewing passageway along the length thereof, means securing said inner tube in fixed position interior of said outer tube with the outer surface of said inner tube spaced a distance radially inwardly from the inner surface of said outer tube.

2. An endoscope as defined in claim 1 wherein said securing means include spacers located between said outer tube and said inner tube, the surface of said spacers in engagement with said tubes being small in comparison with the facing surface areas of said tubes.

3. An endoscope as defined in claim 2 wherein said spacers are ring shaped.

4. An endoscope as defined in claim 2 wherein said spacers have a pointed profile.

5. An endoscope as defined in claim 2 wherein said spacers are ring segments.

6. An endoscope as defined in claim 2 wherein at least one of said spacers are formed as an integral part of said outer tube.

7. An endoscope as defined in claim 2 wherein at least one of said spacers are formed as an integral part of said inner tube.

8. An endoscope as defined in claim 1 wherein the outer surface of said outer tube is coated with a thin layer of materials whose index of refraction is lower than the index of refraction of the material of said outer tube.

9. An endoscope as defined in claim 1 wherein the inside wall of said outer tube and the outside wall of said inner tube are slightly conical, with the larger diameter at the proximal end thereof, and wherein the contact areas of said inner and outer tubes are dimensioned such that said inner and outer tubes are self-locking.

10. A speculum for use with an endoscope head of the type having an illumination means for directing light into a tubular speculum, said speculum comprising a rigid outer tube of light conducting material having a distal end and a proximal end, said proximal end being adapted to be secured to said endoscope head and to receive light from said endoscope head, said distal end being adapted to be inserted into a body cavity, said outer tube conducting light from said proximal end to said distal end to illuminate said body cavity while permitting the passage of unwanted transverse light intermediate said proximal and distal ends, an inner tube defining viewing passageway and being dimensioned to permit observation of the interior of said body cavity therethrough, said inner tube being of a material such that it prevents extraneous light from entering said viewing passageway along the length thereof, means securing said inner tube in fixed position interior of said outer tube with the outer surface of said inner tube spaced a distance radially inwardly from the inner surface of said outer tube.

* * * * *